US011766223B1

(12) United States Patent
Vaghefi Rezaei et al.

(10) Patent No.: US 11,766,223 B1
(45) Date of Patent: Sep. 26, 2023

(54) SYSTEMS AND METHODS FOR PROCESSING OF FUNDUS IMAGES

(71) Applicant: TOKU EYES LIMITED, Auckland (NZ)

(72) Inventors: Seyed Ehsan Vaghefi Rezaei, Auckland (NZ); David Squirrell, Auckland (NZ); Song Yang, Auckland (NZ); Songyang An, Auckland (NZ); Li Xie, Auckland (NZ)

(73) Assignee: TOKU EYES LIMITED, Newmarket (NZ)

( * ) Notice: Subject to any disclaimer, the term of this patent is extended or adjusted under 35 U.S.C. 154(b) by 0 days.

(21) Appl. No.: 18/050,782

(22) Filed: Oct. 28, 2022

Related U.S. Application Data

(60) Provisional application No. 63/364,249, filed on May 5, 2022.

(51) Int. Cl.
*G06K 9/00* (2022.01)
*A61B 5/00* (2006.01)
(Continued)

(52) U.S. Cl.
CPC .............. *A61B 5/7275* (2013.01); *A61B 3/12* (2013.01); *A61B 5/486* (2013.01); *A61B 5/7221* (2013.01);
(Continued)

(58) Field of Classification Search
CPC .. A61B 5/486; A61B 3/12; A61B 3/14; A61B 5/14555; A61B 5/02;
(Continued)

(56) References Cited

U.S. PATENT DOCUMENTS

2020/0027209 A1* 1/2020 Madabhushi ............. G06T 5/20
2020/0202527 A1* 6/2020 Choi ...................... G06V 10/82
(Continued)

*Primary Examiner* — Atiba O Fitzpatrick
(74) *Attorney, Agent, or Firm* — Knobbe, Martens, Olson & Bear, LLP

(57) ABSTRACT

Systems and methods for predicting a risk of cardiovascular disease (CVD) from one or more fundus images are disclosed. Fundus images associated with an individual are processed to determine whether fundus images are of sufficient quality. The fundus images of sufficient quality are processed to identify fundus images belonging to a single eye. A plurality of risk contributing factor sets of CNNs (RCF CNN) are configured to output an indicator of probability of the presence of a different risk contributing factor in each of the one or more fundus images. At least one of the RCF CNNs is configured in a jury system model having a plurality of jury member CNNs, each being configured to output a probability of a different feature in the one or more fundus images. The outputs of the jury member CNNs are processed to determine the indicator of probability of the presence of the risk contributing factor output by the RCF CNN. An individual feature vector is produced based on meta-information for the individual, and the outputs of the RCF CNNs. The individual feature vector is processed using a CVD risk prediction neural network model to output a prediction of overall CVD risk for the individual. The model is configured to determine a relative contribution of each of the risk contributing factors to the prediction of overall CVD risk. The overall CVD risk is reported, together with the relative contribution of each of the risk contributing factors to the overall CVD risk.

20 Claims, 6 Drawing Sheets

(51) Int. Cl.
*A61B 3/12* (2006.01)
*G06V 10/40* (2022.01)
*G06T 7/00* (2017.01)

(52) U.S. Cl.
CPC .......... *A61B 5/7246* (2013.01); *A61B 5/7264* (2013.01); *G06T 7/0014* (2013.01); *G06V 10/40* (2022.01); *G06T 2207/10024* (2013.01); *G06T 2207/20084* (2013.01); *G06T 2207/30041* (2013.01); *G06V 2201/10* (2022.01)

(58) Field of Classification Search
CPC ... A61B 5/02028; A61B 5/0205; A61B 5/021; A61B 5/024; A61B 5/02405; A61B 5/7275; A61B 5/7221; A61B 5/7246; A61B 5/7264; G06T 2207/30041; G06T 2207/30048; G06T 2207/30101; G06T 7/0012–0016; G06T 2207/10064–10136; G06T 2207/30004–30104; G06T 2207/20081; G06T 2207/20084; G06T 7/0014; G06T 2207/10024; G06V 2201/031; G06V 10/87; G06V 30/19113; G06V 2201/03–034; G06V 10/70; G06V 10/82; G06V 10/774–7796; G06V 10/40; G06V 2201/10; G16H 30/40; G16H 50/20; G16H 50/30; G06N 20/20; G06N 3/0454; G06N 3/02–126; G06N 20/00–20; G06K 9/6256; G06K 9/6257; G06K 9/6259; G06F 18/214–2155; G06F 7/023; G06F 40/16

See application file for complete search history.

(56) References Cited

U.S. PATENT DOCUMENTS

| | | | |
|---|---|---|---|
| 2020/0405148 A1* | 12/2020 | Tran | A61B 3/0016 |
| 2021/0378510 A1* | 12/2021 | Park | A61B 3/0025 |
| 2022/0175325 A1* | 6/2022 | Fukushima | G16H 50/30 |
| 2022/0301709 A1* | 9/2022 | Choi | A61B 5/021 |
| 2022/0378378 A1* | 12/2022 | Cho | A61B 5/7267 |
| 2023/0077125 A1* | 3/2023 | Chiou | G06T 7/11 |

* cited by examiner

Plot of ORA/CLE predicted risk for UK Biobank test set

Plot of ORA/CLE predicted risk for AREDS 1

SYSTEMS AND METHODS FOR PROCESSING OF FUNDUS IMAGES

CROSS-REFERENCE TO RELATED APPLICATION

This application is based on U.S. patent application Ser. No. 63/364,249, filed May 5, 2022, and Australian patent application no. 2022901625, filed Jun. 15, 2022, the entire contents of which are incorporated herein by reference.

TECHNICAL FIELD

The present technology relates to systems and methods for processing fundus images, more particularly the processing of fundus images to determine a risk level of cardiovascular disease (CVD).

BACKGROUND

Cardiovascular disease (CVD) is the leading cause of hospitalisation and premature death in the USA, and its most common comorbidities include non-modifiable factors such as age and gender, and modifiable factors such as glycaemic control, blood pressure, cholesterol, and exposure to smoking.

National CVD risk management guidelines recommend that treatment decisions should be informed by their predicted CVD risk. CVD risk varies greatly across a population (from minimal to severe), and identification of personal CVD risk using current statistical methods has issues with accuracy. The modest accuracy of current CVD risk prediction equations (i.e. resulting in too many false positives and false negatives) is largely because the available predictors are all indirect measures of CVD. These equations use regression models applying parameters such as age, sex, ethnicity, socioeconomic deprivation, smoking, diabetes duration, systolic blood pressure, total cholesterol-to-HDL ratio, glycated haemoglobin A1c (HbA1c), and urine albumin-to-creatinine ratio (ACR). More accurate CVD risk stratification is needed to better target medications and treatment program to appropriate recipients.

The retina is the only part of the human vasculature that is directly visible by non-invasive means. Several studies have recently shown that an artificial intelligence (AI) deep learning retinal image algorithm can be used for estimating CVD risk. However, in all of these methods, the retinal images are trained against a single label. Some studies have used the chronological age as the "label" for training, and the outcome of the model is called "retinal age". Any discrepancies between the label (chronological) and estimated (retinal) ages is considered as an indication of higher risk of CVD event. Other studies have used the CVD risk calculated by conventional equations as the "label". In this approach, the outcome is a single number (presumably perceived risk), which has proven to be inaccurate. Furthermore, neither of these approaches identify the major contributors of the CVD risk (e.g. blood pressure vs cholesterol vs glycaemic control vs other contributors).

It is an object of the present disclosure to address at least one of the foregoing problems or at least to provide the public with a useful choice.

Further aspects and advantages of the present disclosure will become apparent from the ensuing description which is given by way of example only.

SUMMARY

The present technology provides systems and methods for retinal image analysis using artificial intelligence (AI). Because retinal images, also referred to as fundus images, are routinely taken as part of medical screening procedures (for example, retinal screening for diabetic retinopathy), these images have the potential to be rapidly analysed at low cost for improving CVD risk prediction, and made available immediately to the patient and their health care provider with no additional burden to the patient.

According to one aspect of the present technology there is provided a method of predicting a risk of cardiovascular disease (CVD) from one or more fundus images, the method performed by one or more processors. In examples the method comprises processing one or more fundus images associated with an individual using a Quality Assurance (QA) set of one or more convolutional neural networks (CNNs) to determine whether the one or more fundus images are of sufficient quality for further processing. In examples the method further comprises processing the one or more fundus images determined to be of sufficient quality for further processing using an eye-identification set of one or more CNNs (eye-ID CNN), to identify the one or more fundus images belonging to a single eye. In examples the method further comprises processing the one or more fundus images using a plurality of risk contributing factor sets of one or more CNNs (RCF CNN), wherein each RCF CNN is configured to output an indicator of probability of the presence of a different risk contributing factor in each of the one or more fundus images, wherein at least one of the RCF CNNs is configured in a jury system model comprising a plurality of jury member CNNs, wherein each jury member CNN is configured to output a probability of a different feature in the one or more fundus images, and the outputs of the plurality of jury member CNNs are processed to determine the indicator of probability of the presence of the risk contributing factor output by the RCF CNN. In examples the method further comprises producing an individual feature vector based on meta-information for the individual, and the outputs of the plurality of RCF sets of one or more CNNs. In examples the method further comprises processing the individual feature vector using a CVD risk prediction neural network model to output a prediction of overall CVD risk for the individual, wherein the CVD risk prediction neural network model is configured to determine a relative contribution of each of the risk contributing factors to the prediction of overall CVD risk. In examples the method further comprises reporting the overall CVD risk, comprising reporting the relative contribution of each of the risk contributing factors to the overall CVD risk.

According to one aspect of the present technology there is provided a method of predicting cardiovascular disease (CVD) from one or more fundus images, the method performed by one or more processors, the method comprising: processing one or more fundus images associated with an individual using a plurality of sets of one or more convolutional neural networks (CNNs). In examples the plurality of sets of one or more CNNs may include two or more of: a Quality Assurance (QA) set of one or more CNNs, an eye-identification (eye-ID) set of one or more CNNs, a localized change set of one or more CNNs, a global change set of one or more CNNs, and a metarepresentation set of one or more CNNs.

According to one aspect of the present technology there is provided a system comprising a memory storing program instructions; and at least one processor configured to execute program instructions stored in the memory, wherein the program instructions cause the processor to perform the method of predicting cardiovascular disease (CVD) described herein.

According to one aspect of the present technology there is provided a computer program product, the computer program product comprising: a non-transitory computer-readable medium having computer-readable program code stored thereon, the computer-readable program code comprising instructions that when executed by a processor, cause the processor to perform the method of predicting cardiovascular disease (CVD) described herein.

According to one aspect of the present technology there is provided a method of predicting cardiovascular disease (CVD) from one or more fundus images, the method performed by one or more processors, the method comprising:

processing one or more fundus images associated with an individual using a plurality of risk contributing factor (RCF) sets of one or more CNNs, wherein each RCF set of one or more CNNs is configured to output an indicator of probability of the presence of a different risk contributing factor in each of the one or more fundus images;

producing an individual feature vector based on meta-information for the individual, and the outputs of the plurality of RCF sets of one or more CNNs;

processing the individual feature vector using a CVD risk prediction neural network model to output a prediction of CVD risk for the individual.

According to one aspect of the present technology there is provided a method of predicting a risk of cardiovascular disease (CVD) from one or more fundus images, the method performed by one or more processors, the method comprising:

processing one or more fundus images associated with an individual using a Quality Assurance (QA) set of one or more CNNs to determine whether the one or more fundus images are of sufficient quality for further processing;

processing the one or more fundus images determined to be of sufficient quality for further processing using an eye-identification (eye-ID) set of one or more CNNs, to identify the one or more fundus images belonging to a single eye;

processing the one or more fundus images using a plurality of risk contributing factor (RCF) sets of one or more CNNs, wherein each RCF set of one or more CNNs is configured to output an indicator of probability of the presence of a different risk contributing factor in each of the one or more fundus images;

producing an individual feature vector based on meta-information for the individual, and the outputs of the plurality of RCF sets of one or more CNNs;

processing the individual feature vector using a CVD risk prediction neural network model to output a prediction of CVD risk for the individual.

In examples, the one or more fundus images may be processed using a Quality Assurance (QA) set of one or more convolutional neural networks to determine whether the one or more fundus images are of sufficient quality for further processing.

In examples, classifying an image as unsuitable may comprise determining that the image is not directed to a relevant region of an eye of the individual. In examples, determining the image is unsuitable may comprise determining that at least one property of the image is unsuitable. For example, the image may be determined as being over-saturated, underexposed, out of focus, or blurred.

In examples, a notification may be issued warning a user that the one or more fundus images supplied are unsuitable. This enables one or more replacement images to be supplied.

In examples the one or more fundus images may be adjusted prior to processing. In examples, the image adjustment may be normalisation of the images, for example spatial or intensity normalisation. In examples, spatial normalisation may include one or more of: cropping, scaling, and rotation of the one or more fundus images.

In examples, a color balancing process may be performed on the one or more fundus images. In an example, a Gaussian filter may be applied to the one or more fundus images in order to perform color balancing. Image quality, as it pertains to color, can vary significantly between different fundus camera technologies and/or models. Colour balancing reduces the mismatch in images resulting from this, to assist with further processing. In examples, the one or more fundus images may be converted from a colour image into a greyscale or monochrome image.

In examples, a brightness adjustment process may be performed on the one or more fundus images. Image brightness can greatly vary due to environmental conditions (for example, lighting within a clinic) and patient pupil size. Brightness adjustment normalizes these variations to assist with further processing.

In examples in which the one or more fundus images comprises a plurality of fundus images, the plurality of fundus images may be processed using an eye-identification (eye-ID) set of one or more convolutional neural networks configured to group the fundus images as belonging to a single eye—for example, for future clinical results aggregation. In examples the eye-ID CNN operates by identifying an eye as left-eye or right-eye, understanding the "likeness" of several images, and one or more parameters including, but not limited to, image time stamp and patient unique ID. A grouping of images may be referred to as an image set.

In examples, one or more CNNs may be configured to identify a relative location of the one or more fundus images on the retina. For example, the one or more CNNs may be configured to determine whether the one or more fundus images are macula-centred or disk-centred. The two main landmarks of the retina are the macula, which has the densest photoreceptor concentration and is responsible for central vision, and the disk, where the optic nerve enters the eye. In examples, the eye-ID CNNs may be configured to identify a relative location of the one or more fundus images on the retina.

In examples, one or more CNNs may be configured to determine a device, or characteristic of the device, used to capture the fundus image. In examples the one or more CNNs may be configured to determine whether the device utilises flash photography or white LED confocal photography. In examples, processing of the fundus image may be based at least in part on determination of the device, or the characteristic of the device. In examples, adjustment of the one or more fundus images prior to processing may be based at least in part on the determination of the device, or the characteristic of the device.

In examples, the one or more fundus images are processed by a plurality of risk contributing factor (RCF) sets of one or more CNNs, each RCF set of one or more CNNs configured to output an indication of the probability of the presence of a different risk contributing factor. In examples, the risk contributing factors may include two or more of: glycaemic control, blood pressure, cholesterol, and exposure to smoking. In examples, each of the CNNs may produce a probability of an indicator of this risk contributing factor. For example, the CNNs may look for "localized" signs of biological changes and physiological changes (e.g. microaneurysms, oedema, etc.) changes, and or "global" changes in an image that could indicate presence of glycaemic control, blood pressure, cholesterol, and exposure to smoking (e.g.

pigmentary changes in the peripapillary region, arterial/venous crossing deformations, vascular tortuosity changes, vascular calibre changes, etc.). In examples the signs may include, but not be limited to: drusen appearance, clustering, and/or location; pigmentation change in density and/or location; arteriovenous crossing; change in arteriovenous crossing calibre and/or thickness change; arteriovenous tortuosity; retinal oedema size and/or pattern; and/or microaneurysms concentration.

In examples, at least one of the RCF CNNs may be configured in a jury system model comprising a plurality of jury member CNNs, wherein each jury member CNN is configured to output a probability of a different feature in the one or more fundus images, and the outputs of the plurality of jury member CNNs are processed to determine the indicator of probability of the presence of the risk contributing factor output by the RCF CNN.

For example, investigation of each risk contributing factor (e.g. glycaemic control, blood pressure, cholesterol, and exposure to smoking) may include a plurality (for example, at least five) of jury members. Each jury member may be configured to output a probability. The jury system model may produce a final probability based on the outcomes from each jury member. In examples the outputs of the plurality of jury member CNNs may be processed to determine the indicator of probability of the presence of the risk contributing factor output by the RCF CNN based on an expected population baseline for a population to which the individual belongs.

In examples, the outputs from the risk contributing factor (RCF) sets of one or more CNNs are aggregated using minimum, maximum, mean, and median in both model-level and image-level to generate an individual-level fundus image feature vector. In examples, the raw output of each model may be several floating values, where the length of output is model-dependent. The output aggregation firstly happens on a model-level. For example, for an input fundus image, five juror models give probabilities from 0 to 1, i.e. a minimum of 0 and a maximum of 1 (e.g. a decimal value such as 0.01454), and the probabilities for each grade level across five models are also aggregated. In examples, the output of the models are floating-point numbers and after the aggregation using a mathematical operation (including, but not limited to, weighted mean, min, max, etc.), the final output is still in the form of floating numbers. In examples, these floating-point numbers, are concatenated to form a one-dimensional array (i.e. the individual-level fundus image feature vector). In examples, meta-information of an individual associated with the one or more fundus images is combined with the individual-level fundus image feature vector to produce an individual feature vector. In examples a meta-information vector is produced from the meta-information. In examples, the meta-information is pre-processed using one or more of standardisation and one-shot encoding. For example, numerical feature such as age may be standardised to have a mean 0 and standard variance 1. For example, categorical features (e.g. gender and ethnicity) may be converted from string data to numerical vectors using one-shot encoding. In examples, the individual-level fundus image feature vector and the meta-information vector may be concatenated to produce the individual feature vector. This provides a metarepresentation understandable by neural networks.

In examples the CVD risk prediction neural network model utilises a fully connected neural network (FCNN). In examples the FCNN may have at least 5 layers. In examples, the relative contribution of each modifiable factor (e.g. glycaemic control, blood pressure, cholesterol, and exposure to smoking) to the overall CVD risk score is determined. This combination is not an equation, but rather an algorithmic approach, where the patient biometrics are combined and weighted appropriately with their retinal images, within the deeper layers of the overall FCNN design.

In examples, the functionality of two or more of the respective sets of one or more convolutional neural networks disclosed herein may be provided by a single set of one or more convolutional neural networks.

In examples, the system may be configured to report CVD risk on one or more of: an individual level, and a population level. At an individual level, an individual overall CVD risk may be reported—i.e. the overall risk of CVD to an individual associated with processed fundus images. In examples, the system may be configured to report on the contributing factors to the individual overall CVD risk, including non-modifiable contributing factors (e.g. based on patient meta-information such as age, gender, and/or ethnicity) and modifiable contributing factors (e.g. based on glycaemic control, blood pressure, cholesterol, and exposure to smoking). In examples the system may be configured to identify the relative contribution of the respective modifiable contributing factors. In examples the system may be configured to rank the modifiable contributing factors according to their relative contribution to the individual overall CVD risk.

At a population level, the system may be configured to report analysis is presented where the overall cohort cardiovascular risk profile and its contributing factors are generated. By way of example, the cohort may be that a population at local, regional, or national levels, the population of a healthcare provider, that of an organisation, or subsets thereof (for example, risk levels within the overall population). Similarly to the individual overall CVD risk, the system may be configured to report on the respective relative contributions of modifiable contributing factors at a population level.

In examples, the system may be configured to provide a recommendation for management of an individual's condition based on the determined risk. For example, a scale of risk levels may be provided, each risk level having an associated recommendation. In examples, at least one recommendation may be provided based on the relative contribution of each modifiable contributing factor. Such recommendations may relate to one or more of: lifestyle (e.g. diet and exercise), further clinical assessments (e.g. cardiologist consultation), or medication (e.g. adherence) decisions.

In examples, the results could be sent to an agency for further analysis, e.g. a healthcare payer for population health analysis.

In examples, the system may be configured to compare at least one of the overall CVD risk, and the relative contribution of each of the risk contributing factors to the overall CVD risk, of the individual to at least a portion of a population of individuals for whom the overall CVD risk is predicted by the CVD risk prediction neural network model, and report an indication of the comparison.

In examples, the system may be configured to predict a change to the overall CVD risk based on a change to one or more of the risk contributing factors. In examples the system may be configured to predict a group overall CVD risk for at least a portion of a population of individuals for whom the overall CVD risk is predicted by the CVD risk prediction neural network model. In examples, the system may be configured to predict a change to the group overall CVD risk based on a change to one or more of the risk contributing factors for at least a portion of the population of individuals.

The above and other features will become apparent from the following description and the attached drawings.

BRIEF DESCRIPTION OF THE DRAWINGS

Further aspects of the present disclosure will become apparent from the following description which is given by way of example only and with reference to the accompanying drawings in which.

DETAILED DESCRIPTION

Figure 1:
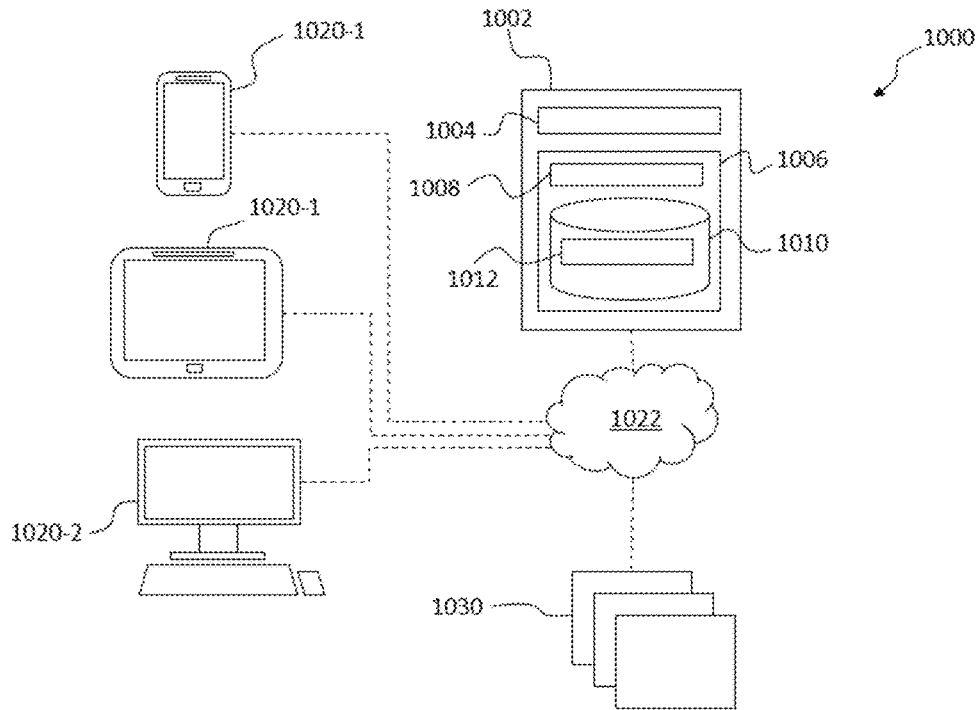
FIG. 1 is a schematic diagram of a system depicting various computing components that can be used alone or together in accordance with aspects of the present technology.

FIG. 1 presents a schematic diagram of a system 1000 depicting various computing components that can be used alone or together in accordance with aspects of the present technology. The system 1000 comprises a processing system 1002. By way of example, the processing system 1002 may have processing facilities represented by one or more processors 1004, memory 1006, and other components typically present in such computing environments. In the exemplary embodiment illustrated the memory 1006 stores information accessible by processor 1004, the information comprising instructions 1008 that may be executed by the processor 1004 and data 1010 that may be retrieved, manipulated or stored by the processor 1004. The memory 1006 may be of any suitable means known in the art, capable of storing information in a manner accessible by the processor, comprising a computer-readable medium, or other medium that stores data that may be read with the aid of an electronic device. The processor 1004 may be any suitable device known to a person skilled in the art. Although the processor 1004 and memory 1006 are illustrated as being within a single unit, it should be appreciated that this is not intended to be limiting, and that the functionality of each as herein described may be performed by multiple processors and memories, that may or may not be remote from each other.

The instructions 1008 may comprise any set of instructions suitable for execution by the processor 1004. For example, the instructions 1008 may be stored as computer code on the computer-readable medium. The instructions may be stored in any suitable computer language or format. Data 1010 may be retrieved, stored or modified by processor 1004 in accordance with the instructions 1008. The data 1010 may also be formatted in any suitable computer readable format. Again, while the data is illustrated as being contained at a single location, it should be appreciated that this is not intended to be limiting—the data may be stored in multiple memories or locations. The data 1010 may comprise databases 1012.

In some embodiments, one or more user devices 1020 (for example, a mobile communications capable device such as a smartphone 1020-1, tablet computer 1020-2, or personal computer 1020-3) may communicate with the processing system 1000 via a network 1022 to gain access to functionality and data of the processing system 1002. The network 1022 potentially comprises various configurations and protocols comprising the Internet, intranets, virtual private networks, wide area networks, local networks, private networks using communication protocols proprietary to one or more companies—whether wired or wireless, or a combination thereof. For example, fundus images obtained from one or more fundus imaging devices (herein referred to as a "fundus camera" 1030) may be input to the processing system 1002 via the user devices 1020.

A fundus camera typically comprises an image capturing device, which in use is held close to the exterior of the eye and which illuminates and photographs the retina to provide a 2D image of part of the interior of the eye. Many clinically important regions of the eye may be imaged, comprising the retina, macula, fovea, and optic disc. A single fundus image of a non-dilated eye captures less than 45° of the back of the eye. In practice, a clinician will often choose to capture several photographs while guiding the patients to look up, down, left and right, to create a larger field of view of the retina.

Figure 2A:
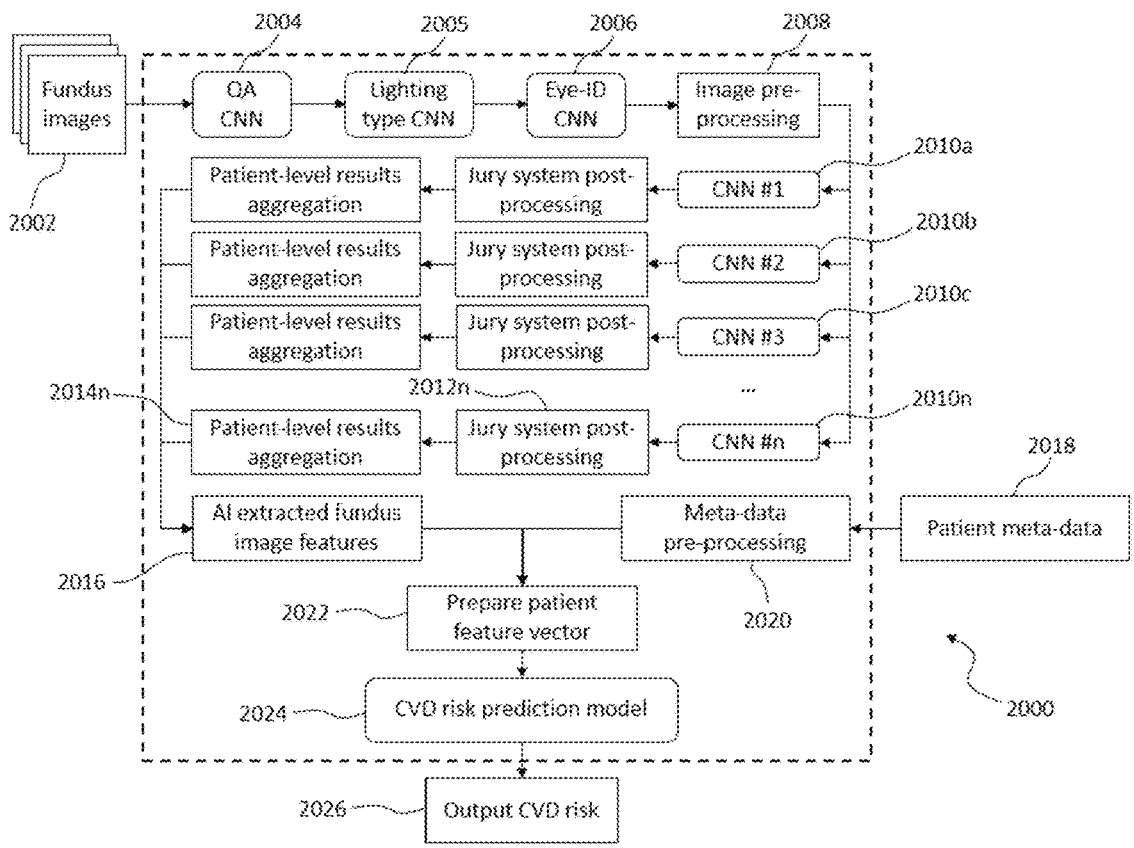
FIG. 2A is a diagram showing a system design describing the flow of processing fundus images to predict a risk of cardiovascular disease (CVD) in accordance with aspects of the present technology.

FIG. 2 illustrates a method/process architecture 2000 for processing fundus images in accordance with aspects of the present technology. For completeness, it will be appreciated that the deep learning models and frameworks disclosed herein are provided by way of example, and that viable alternatives will be apparent to the skilled addressee.

The method 2000 utilises various convolutional neural networks ("CNN"). CNNs are deep learning architectures particularly suited to analysing visual imagery. A typical CNN architecture for image processing consists of a series of convolution layers, interspersed with pooling layers. The convolution layers apply filters, learned from training data, to small areas of the input image in order to detect increasingly more relevant image features. A pooling layer downsamples the output of a convolutional layer to reduce its dimensions. The output of a CNN may take different forms depending on the application, for example one or more probabilities or class labels.

The first dataset for use as training data included measurements from non-diabetic and diabetic patients. Because not all measurements are related to the CVD risk, irrelevant columns were discarded according to the expert advice. As a result, 35 columns corresponding to 21 fields remained, including: age, sex, ethnicity, deprivation score, family history, smoking, systolic blood pressure, BMI, TC/HDL, HbA1c, state of diabetes (Y/N), diabetic type, atrial fibrillation, antihypertensives, antithrombotic medication, lipid lowering medication, eGFR, metolazone prior 6 months, lipids in prior 6 months, LLD prior 6 months, anticoagulation medication prior 6 months, antiplay prior 6 months, CVD event and date, etc. It should be noted that these columns were retained based on the expert's opinion to not miss any helpful variables, but this does not necessitate that all of them should be used in modelling. For the total visits, each patient usually has multiple visits over time (i.e. multiple sets of biometric information may exist for a single patient). Based on expert's advice and to make the study observation time as long as possible, the first visit only for each patient was retained. The resulting first dataset, following the screening process described below, contained 95,992 images from 51,956 patients. A second dataset was created, using the screening process described below, containing 14,280 images from 3,162 patients. This second dataset was used for tuning and validation of the models developed with the training data above.

Figure 3:
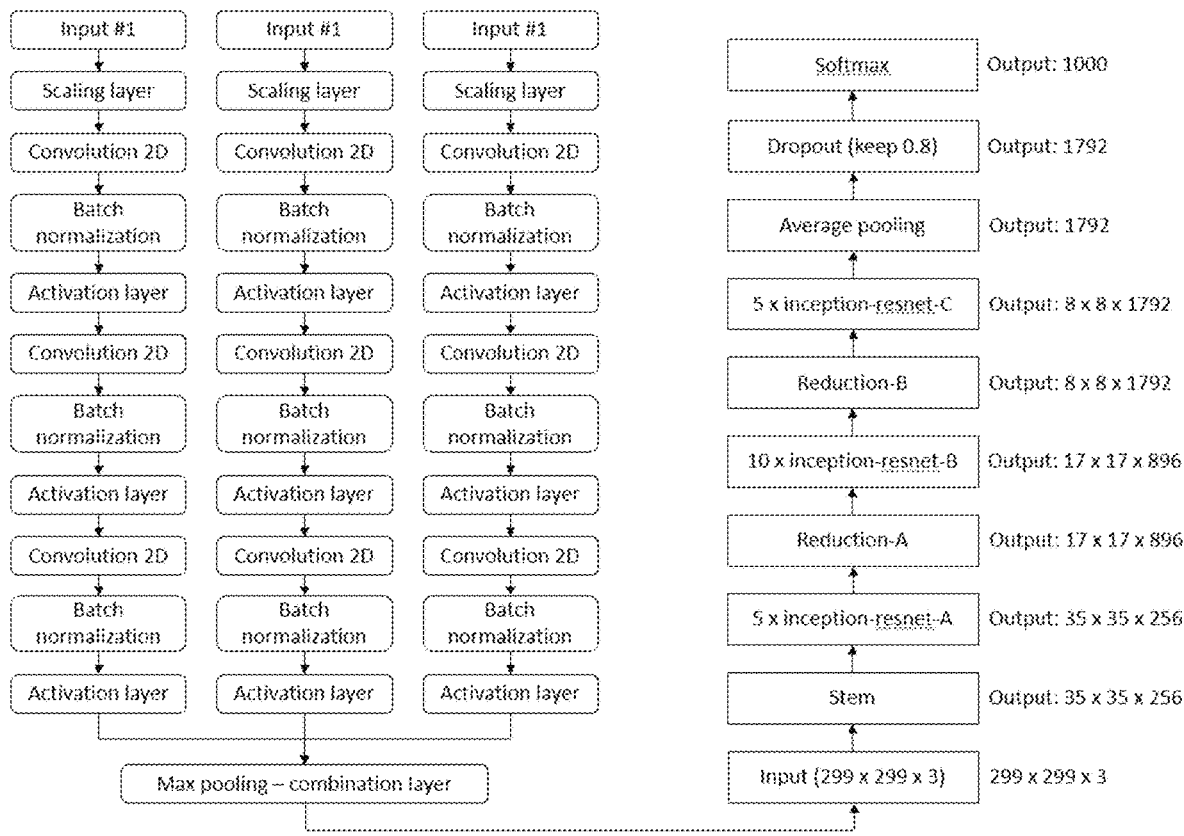
FIG. 3 shows a diagram of an exemplary architecture for a convolutional neural network (CNN) utilised in accordance with aspects of the present technology.

As an example, a modified Inception-ResNet-v2 CNN architecture shown in FIG. 3 may be implemented. Inception-ResNet-v2 is a convolutional neural architecture that builds on the Inception family of architectures but incorporates residual connections. It consists of 164 layers and dozens of inception-residual blocks. Each inception-residual block is made of several parallel branches where different size of convolutional kernel and stride is applied. For example, one branch goes to 1*1 convolutional operation and others go to 1*7, 7*1, 1*3, 3*1, or 3*3. The different size of convolutional kernels intended to capture the image features in the different perspectives. Residual connections are designed to build the deeper network. The idea of residual connection is relatively simple: add the input of each block to the output of the block to preserve the input information. This allows the model to be able to ignore some blocks if necessary and helps the gradients propagation along the network. In examples of the present technology the Inception-ResNet-v2 is used as the feature extractor, and the final layer is adapted to meet the requirements of the present technology, creating a probability of the presence of the learnt feature.

Returning to FIG. 2, at input stage 2002 one or more fundus images are received—for example a collection of fundus photographs of an individual. Quality assurance is performed on the received images to confirm their suitability for further processing. In examples, the quality assurance is performed by a set of one or more quality assurance ("QA") CNNs 2004.

QA CNNs

The QA CNNs 2004 are trained by inputting sample images previously labelled by an expert clinician, and training them for sufficient iterations. In an example, a QA CNN was based on a modified XCEPTION design (although it is noted that a modified Inception-ResNet-v2 design as described above may be utilised), and trained using a dataset of 20,000 images, wherein the dataset comprised similar proportions of four types of images: Type 1: Eyeballs, rooms or other irrelevant images; Type 2: Severely over-saturated or underexposed images; Type 3: Less than perfect images that could still be useful to a clinician in conducting a manual analysis; and Type 4: High quality images.

Experiments were run in an Intel Xeon Gold 6128 CPU @ 3.40 GHz with 16 GB of RAM memory and a NVIDIA GeForce TiTan V VOLTA 12 GB on Windows 10 Professional. Tensorflow 1.11.0 and Python 3.6.6 were utilised to implement the QA CNN 3004 models.

Hyperparameters comprised: (i) Batch Size: 64. Batch size refers to the number of training samples utilised in one step. The higher batch size, the more memory space need. For an input image size of 320*320, and GPU memory of 12 GB, the batch size was set at 64; (ii) Training\validation\testing split: (70\15\15); (iii) Epoch: 100. One epoch refers to one forward pass and one backward pass of all the training examples; (iv) Learning algorithms: the ADAM optimizer was utilised, being an advanced version of stochastic gradient descent; (v) Initial Learning Rate: 10e-3. Learning rate controls how much model adjusting the weights with respect the loss gradient. Typical learning rates are in the order of [10e-1, 10e-5]. In view of use of the ADAM optimizer and batch normalization, the initial learning rate was initially set at 10e-3; (vi) Loss Function: Softmax Cross Entropy; (vii) Dropout rate: 0.5.

The QA CNN described above achieved 99% accuracy in classifying an input image to the categories. Following training, all of the Type 1 and 2 images were removed. Type 3 images are shown to the clinician, but are not used in further processing. Type 4 images are used as part of further processing.

Lighting Type CNNs

In examples, one or more Lighting type CNNs 2005 may be configured to determine a device, or characteristic of the device, used to capture the input fundus image. There are two main photography technologies for fundus imaging: a) flash photography, and b) white LED confocal photography, which produce different looking images. Depending on the camera source (and therefore of the image, the subsequent processing (discussed below) is adjusted.

Eye-ID CNNs

Clinicians often obtain more than one image from a single eye, creating a larger view of the back of the eye. A set of eye-identification (eye-ID) CNNs 2006 are trained to find similarities between several viewpoint images of the same eye, and group them into a single image set. It is important to identify images that belong to the same eye, as a final clinical outcome may be the sum of analysis of each single image in that set.

An exemplary training environment for the eye-ID CNNs 2006 is similar to that described above for the QA CNNs 2004. A database of 160,585 images, from 75,469 eyes of 40,160 people was created. Each image was labelled with Left/Right eye, patient ID (when available) and time stamp of image acquisition. The eye-ID CNNs 2006 were trained on this data set to identify the orientation (Left/Right) of images, and group them based on ID/acquisition time. The trained eye-ID CNNs 2006 achieved more than 99% accuracy. When implemented, the eye-ID CNNs group multiple images submitted by clinician into eye and patient subgroups.

The eye-ID CNNs 2006 are further trained to identify the location of the images on the retina, including identifying the location as being macula-centered or disk-centered.

Image Preparation

Having been processed by the eye-ID CNNs 2006, the fundus images may also be adjusted before further processing at image preparation stage 2008—for example by performing brightness adjustment and colour balancing for normalisation purposes, and cropping and scaling the images for standardisation.

In an example, a Gaussian filter may be applied to the original fundus photo. An example of such a filter may be expressed as:

$$I_c = \alpha I + \beta G(\rho) * I + \gamma$$

where * denotes the convolution operation, I denotes input image and $G(\rho)$ represents the Gaussian filter with a standard deviation of $\rho$. While it will be appreciated that parameters may be optimised for each dataset, an exemplary set of parameters may comprise: alpha=4±1, beta=−4±1, gamma=128±50, ratio=10±10.

Feature Extraction

Next, good quality images with related labels pass through a plurality of AI models. These AI models include sets of risk contributing factor (RCF) CNNs $2010_a$ to $2010_n$ that are trained to detect indicators of: glycaemic control, blood pressure, cholesterol, and exposure to smoking. These indicators include, but are not limited to: drusen appearance, clustering, and/or location; pigmentation change in density and/or location; arteriovenous crossing; change in arteriovenous crossing calibre and/or thickness change; arteriovenous tortuosity; retinal oedema size and/or pattern; and/or microaneurysms concentration.

Figure 2B:
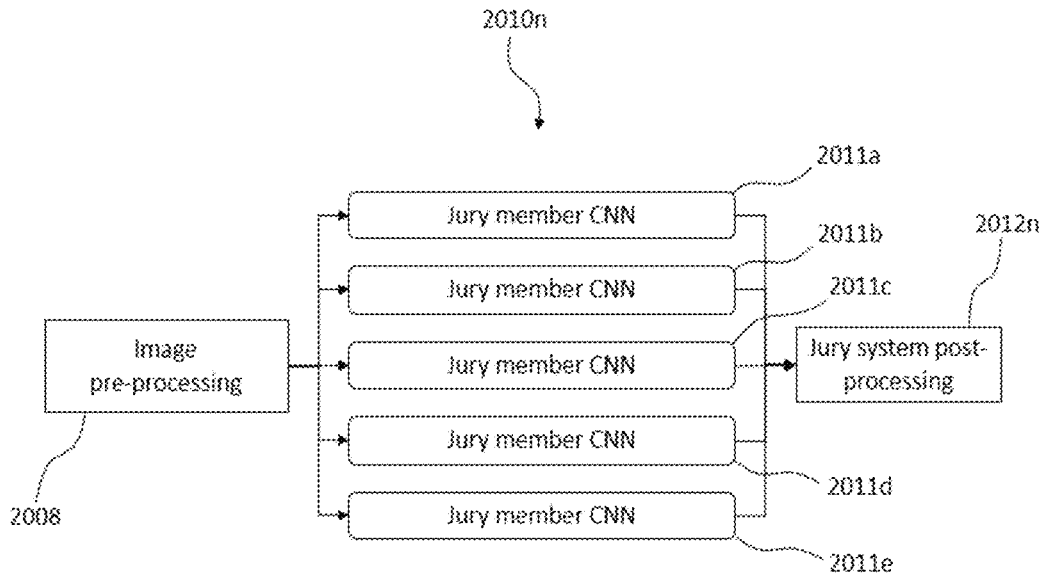
FIG. 2B is a diagram showing a jury model structure of a set of CNNs used in the system in accordance with aspects of the present technology.

The RCF CNNs $2010_a$ to $2010_n$ that are looking for signs of glycaemic control, blood pressure, cholesterol, and exposure to smoking in the retina each act as a "jury" system. Referring to FIG. 2B, each RCF CNN 2010 comprises a plurality of jury member CNNs 2011 (in this example, five jury member CNNs $2011_a$ to $2011_e$), each CNN 2011 configured to produce a probability of the feature it is trained to look at (e.g. the existence and concentration of drusens).

In an exemplary implementation of the CNNs $2010_n$ to extract features from fundus images, 101 layers were stacked with residual connections and inception blocks, resulting in 24,276,481 parameters. A dataset of 95,992 images from 51,956 patients was created. Data points recorded for each patient included: Gender, Date of birth, Date of death if applicable, Ethnicity, socioeconomic deprivation index, HbA1c, SCR, TCHDL, ACR, Blood pressure lowering medicine (Y/N), Lipid lowering medicine (Y/N), antithrombotic medicine (Y/N), oral hypos medicine (Y/N), insulin (Y/N), AF, CVD event, CVD event date, EGFR. The dataset was acquired from multiple eye clinics over 15 years, using several different fundus camera models.

For each CNN $2010_n$ the dataset was then split with a ratio of (70%, 15%, 15%) or similar for training, validation and testing respectively. The fundus images were first cropped and resized to 800×800 (or similar) pixel size. The batch size was set to be 6 to gain maximum utilization of GPU memory in training. Adam optimizer was adopted with learning rate 1*10e-3 to update parameters towards the minimization of the loss. Dropout was enabled with rate p=0.2, and the model was trained for at least 100 epochs. This exemplary implementation was done by Python programming language under version 3.7. A cross-entropy loss function was employed to guide the model parameters optimization. The training objective was to minimize the loss function to get the most accurate probability prediction on a CVD event. Typically, cross-entropy loss is utilized in the context of classification problems. However, although the CVD event risk prediction is not a classification task, the label applied was 1 and 0 (representing whether the CVD event happened or not). Therefore, the cross-entropy loss approach was adopted, with the overall loss being formalized as:

$$L = -\frac{1}{n}\left[\sum_{j=1}^{N} [y_j \log(p_j) + (1 - y_j)\log(1 - p_j)]\right]$$

where N is the number of training samples, v is the ground truth of sample j, and $p_j$ is the predicted probability of CVD risk for sample j. The model performance is also measured by the cross-entropy.

In jury system post-processing 2012, the outcome of each jury member CNN 2011 is then considered, equally or non-equally weighted compared to the rest of the members, to create a statistical representation of the possibility of the changes observed in the particular fundus image.

After receiving the raw outputs from the CNNs $2010_n$, the output results are aggregated at 2014. For example, for an input fundus image, five juror models give probabilities from 0 to 1, i.e. a minimum of 0 and a maximum of 1 (e.g. a decimal value such as 0.01454), and the probabilities for each grade level across five models are also aggregated. In examples, the output of the models are floating-point numbers and after the aggregation using a mathematical operation (including, but not limited to, weighted mean, min, max, etc.), the final output is still in the form of floating numbers concatenated to form a one-dimensional array (i.e. the individual-level fundus image feature vector) at 2016.

In step 2018, examples, meta-information of an individual associated with the one or more fundus images is received. The meta-information includes gender, ethnicity, HbA1c, TCHDL, etc. Some of the meta-information is categorical data such as gender, ethnicity, deprivation value, medicine, etc, and other is numerical data such as age, HbA1c, etc. The meta-information is pre-processed using standardisation and one-shot encoding. After loading this meta-information into memory, the categorical data is converted to one-hot encoding. For example, 3 bits may be used to represent the gender: [1, 0, 0] means male, [0, 1, 0] is female and [0, 0, 1] stands for others. For numerical biometrics, standardization is applied where each value subtracts its mean and divided by the standard deviation to make sure they have same scale— for example, normal HbA1c values range from 30 to 120, while TCHDL values are usually less than 8. As a further example, numerical features such as age may be standardised to have a mean 0 and standard variance 1. This produces a meta-information vector for the individual.

CVD Risk Prediction

After the processing pipelines of fundus images 2016 and meta-information 2020 are completed, the individual-level fundus image feature vector and meta-information vector are concatenated together to form an individual feature vector at step 2022. For example, the meta-information vector may be in the form of [0, 1, 0, 0, 1], and the individual-level fundus image feature vector in the form of [0.3, 0.5, 0.4, 0.35, 0.43, . . . ]. The concatenated vector is [0, 1, 0, 0, 1, 0.3, 0.5, 0.4, 0.35, 0.43, . . . ]. This concatenated vector provides a metarepresentation understandable by neural networks.

The individual feature vector is processed by a CVD risk prediction neural network model 2024 utilising a fully connected neural network (FCNN). In examples the FCNN may have at least 5 layers. The size of each layer (i.e. the number of neurons) is 512, 256, 128, 64, 1 respectively. In an exemplary embodiment a ReLU activation function is used at each layer except the last one. The last layer utilizes a sigmoid function to compress the output to be between [0,1] which serves as the predicted risk/probability.

The model is trained using Adam optimizer with the back propagation algorithm, and cross-entropy loss function to depict the predicted value with the target. The training data includes labels for each individual as to whether they encounter a CVD event (e.g., heart failure) after the fundus images been taken and meta-information has been recorded. Therefore, we can measure the AI model predicted risk with the truth using the cross-entropy loss. If an individual had a CVD event, this means the label is 1. The model prediction 0.6 represents a 1−0.6=0.4 error. If the individual never had a CVD event this means the label is 0, and the model prediction 0.2 indicates the error would be 10-0.21=0.2. Then the average error for each batch is calculated. After having the loss term, the back-propagation method is used to calculate the gradients of each trainable parameter (218,113 parameters in an exemplary model) in terms of the final loss. Then the parameters are updated at the negative gradients direction using Adam algorithm:

$$L = -\frac{1}{m}\sum_{i=1}^{m}(y_i \cdot \log(\hat{y}_i) + (1 - y_i) \cdot \log(1 - \hat{y}_i))$$

The model therefore learns a best set of parameters from the data to minimize the overall loss and gain better prediction results. The relative contribution of each factor toward to the final risk can be estimated using other methods such as controlled experiments. Another method is to "turn on/off" jury member CNNs that are responsible for one aspect (e.g. glycaemic control) and calculate the deviation from the total risk calculated.

In training, a process converts a patient information file into a matrix. The matrix is then converted into a streamed dataset that allows for memory-efficient and time-efficient loading of images. The streamed dataset is then augmented for training purposes. The augmented streamed dataset is then optimized using the gradient descent method via optimizer and loss functions that are provided.

After the pre-processing step, all sorts of available biometrics for each patient are converted to a 1D vector with length 31. Therefore, stacking the feature vector for all patients in the dataset, we will have a feature matrix with shape (44123, 31).

Besides the meta-information, fundus images also need to be pre-processed. After loading the fundus images, the images are re-sized to a pre-defined fixed shape, such as 600*600. Then different image augmentation techniques are employed including randomly adjust brightness, saturation, random flip, rotate, simulate jpeg noise etc.

Because of the large number of images (in an example 95,992 fundus images in total), there are technological limitations preventing loading of all images into memory at once for training. Therefore, the patient's meta-data is transformed with corresponding fundus images into a streamed fashion. In an example, a data generator is created using TensorFlow which produces a mini-batch of data every time. Within each mini-batch, there are several patients visits including the biometrics and fundus images. Then the streamed dataset is fed into the model for training.

The CVD risk prediction neural network model 2024 functions on the underlying recognition that a pattern in a feature of a fundus image (e.g. arterial wall thickening), can be caused for several reasons (i.e. the risk contributing factors such as high blood pressure, high cholesterol, etc)—whether individually or in combination. In other words, one change in the retina cannot be attributed to a single disease, hence the use of probabilities. The 'jury-based' local to global statistical model that represents changes in the retinal photograph is used to estimate a risk for the cardiovascular event within a time period (e.g. 5 to 10 years), and identify the relative contribution of various components of the estimated cardiovascular risk. Here, the jury-based probabilities of the RCF CNNs 2010 are grouped together and assessed against probabilities of changes by non-modifiable factors (e.g. age, race, gender) and modifiable factors (e.g. glycaemic control, blood pressure, cholesterol, and exposure to smoking). In doing so, the CVD risk prediction neural network model 2024 learns if changes to one modifiable factor correlate with changes in other modifiable factors. As an example, in a patient with calculated 20% risk of cardiovascular event in the next 5 years, jury-based estimated probabilities of (i) local changes in arterial wall thickening, and (ii) global colour pattern changes indicate retinal layer thinning, plus probabilities of changes due to age, gender and race are combined to estimate that 8% of the risk are due to non-modifiable factors e.g. (age, race, gender), while from the remaining 12%, 6% is due to high-blood pressure, 3% due to diabetes and the rest split between kidney function and smoking.

CVD Risk Results Presentation

The end output is a prediction of CVD risk capable of being broken down into the contributing factors, including non-modifiable contributing factors (e.g. based on patient meta-information such as age, gender, and/or ethnicity) and modifiable contributing factors (e.g. based on glycaemic control, blood pressure, cholesterol, and exposure to smoking). In one example, this is achieved by individual or group analysis of the relative contribution of CNNs that are responsible for the effects of each factor (e.g. smoking), including an inclusion/exclusion analysis, weight adjustment analysis, and sensitivity analysis.

In examples the system may be configured to rank the modifiable contributing factors according to their relative contribution to the individual overall CVD risk.

Figure 4A:
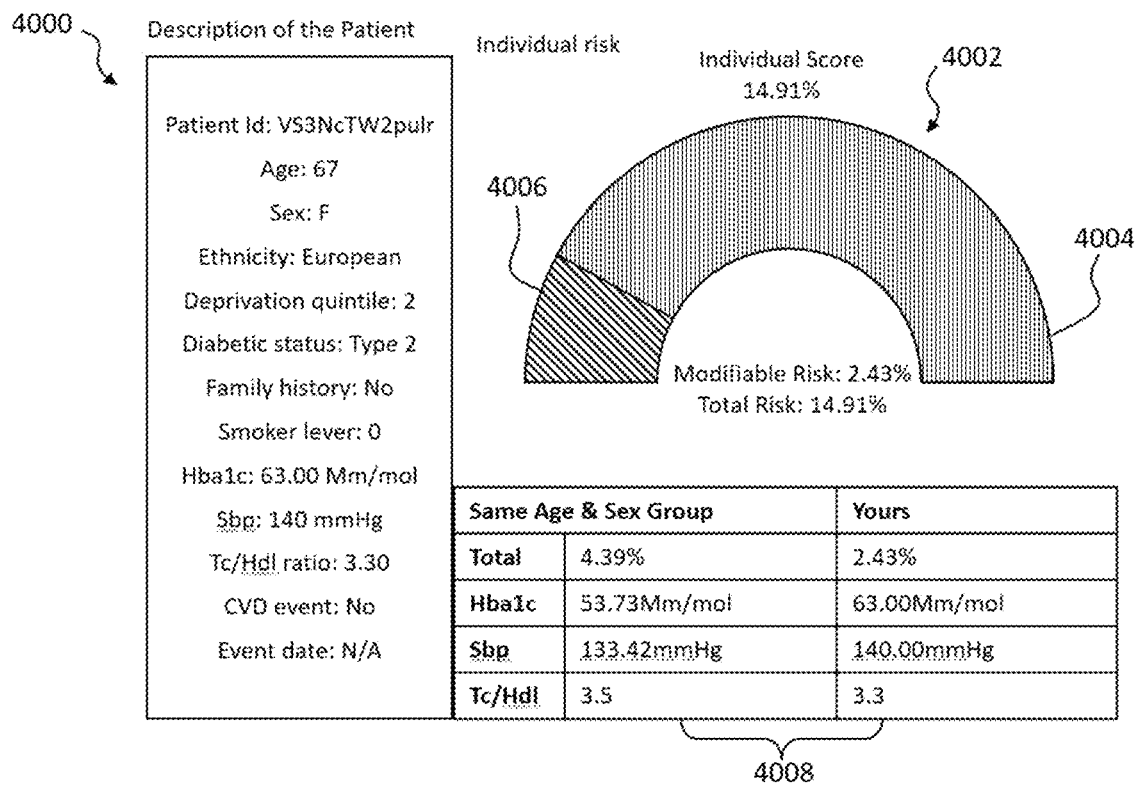
FIG. 4A shows a first exemplary interface displaying individual-level CVD risk information.

FIG. 4A illustrates an individual reporting interface 4000 in which a CVD risk radial gauge 4002 reports an individual's overall risk of CVD, together with the relative contribution of non-modifiable contributing factors 4004 and modifiable contributing factors 4006. In this example, a tabular comparison 4008 is displayed, comparing the individual's results to a comparable population (e.g. within the same age and sex groups).

Figure 4B:
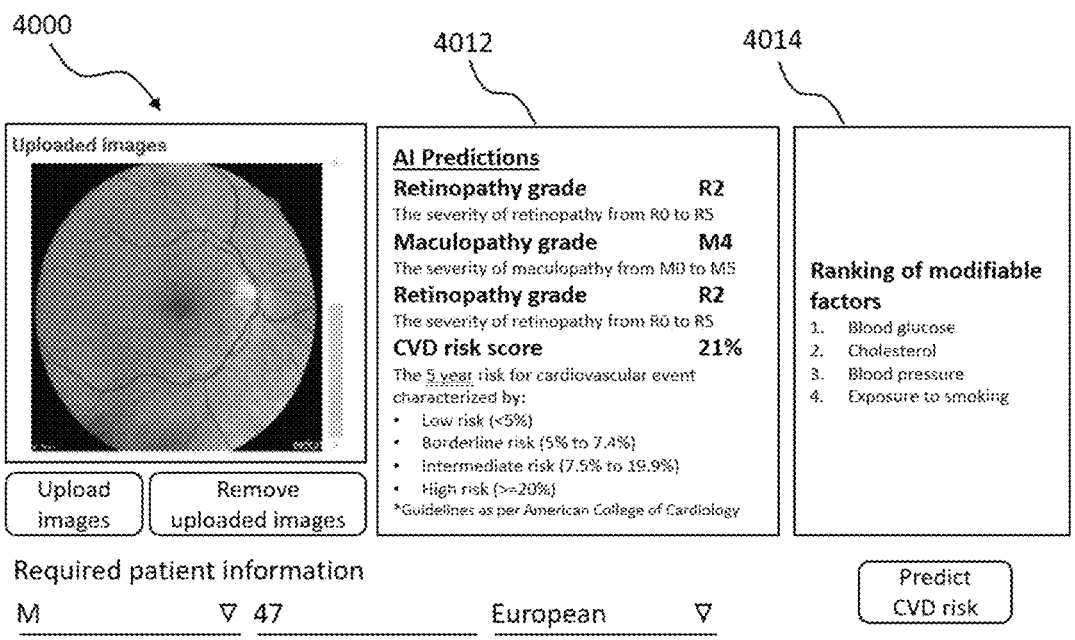
FIG. 4B shows a second exemplary interface displaying individual-level CVD risk information.

FIG. 4B illustrates an alternative individual reporting interface 4010 in which predictions are presented in a predictions pane 4012, and a risk contributions pane 4014 presents a ranked list of the modifiable contributing factors.

These "relative contributions" are then used to provide tailored lifestyle and wellness advice to the screened patient. For example, the CVD risk and relative contributions may be presented in the form:

Overall CVD Risk: 24%

Modifiable factors in the order of relative contribution:

Glycaemic control: 70%

Blood pressure: 10%

Cholesterol: 10%

Non-Modifiable factors relative contribution (age, ethnicity, gender, etc.): 10%

For example, an individual living with diabetes and also suffering from hypertension will have an elevated risk of cardiovascular risk, irrespective of their age, ethnicity and gender. Research indicates that CVD risk can be significantly reduced in this individual if the following advice is adhered to:

Moderate aerobic activity, 75 minutes of vigorous aerobic activity, or an equal combination of moderate and vigorous activity a week.

Eat a healthy diet that emphasizes: Fruits, vegetables and whole grains; Low-fat dairy products and low-fat proteins, such as poultry, fish and legumes; Moderate amounts of healthy fats, such as unsalted nuts, and vegetable and olive oils;

Maintain a healthy weight.

Don't smoke cigarettes or use tobacco.

If you're overweight or obese, lose weight.

Take diabetes medications as recommended by your doctor.

Check your blood sugar and keep it under control as recommended by your doctor.

The process of providing lifestyle advice may be fully automated. The results, which includes the overall CVD risk score, and the main modifiable contributors (i.e. glycaemic control, blood pressure, cholesterol, and exposure to smoking, etc.) may be sent to a healthcare provider for further follow ups. In examples, the results may be utilised by other agencies, for example for population health analysis.

In examples, the system 1000 may be configured to predict the effect of changes to the modifiable contributing factors. For example, where someone has a CVD risk score of 13%, if they were to reduce their HbA1c (an indicator of glycaemic control) by, for example, 20% then the technology would predict that this would allow their CVD risk score to drop, for example to 11%. This predictive element could be based on a single factor change (e.g. HbA1c reduction) or multiple factor changes (e.g. a combination of two or more of HbA1c, cholesterol, and blood pressure reduction).

Figure 4C:
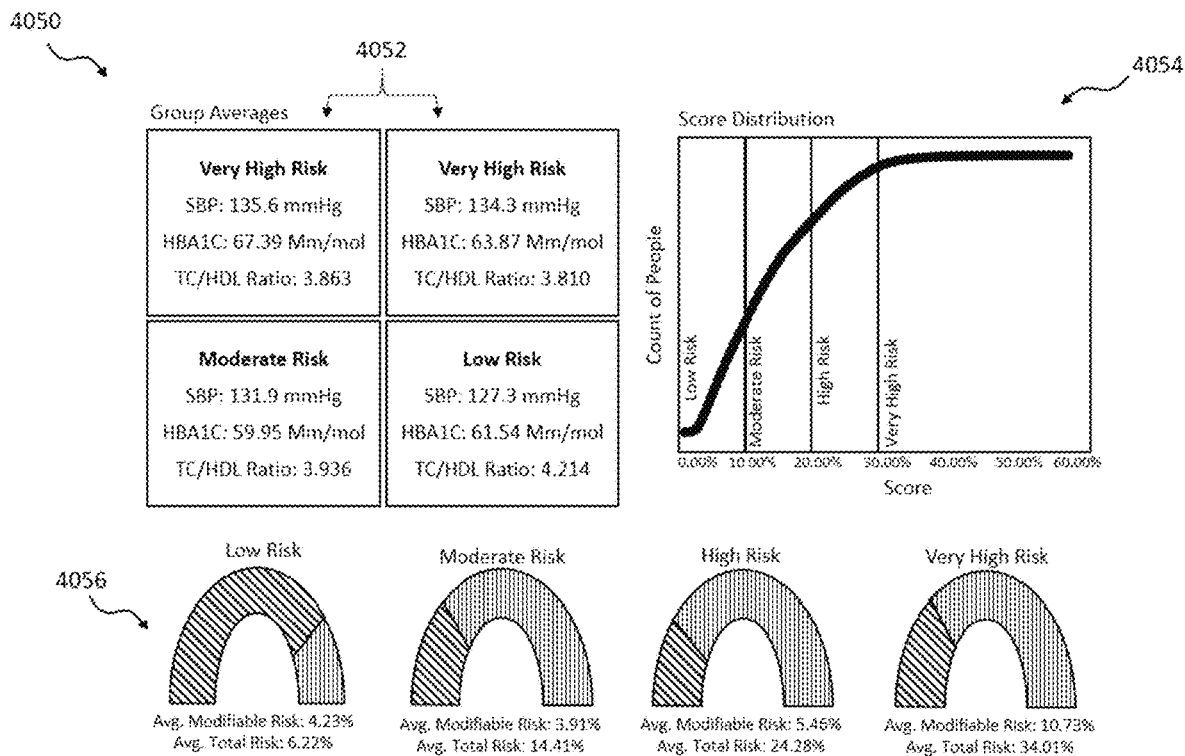
FIG. 4C shows an exemplary interface displaying population-level CVD risk information.

FIG. 4C illustrates an exemplary population reporting interface 4050, where the overall cohort cardiovascular risk profile and its contributing factors are displayed. In this example, the population reporting interface 4050 includes a group average indicators 4052 in various categories of risk; a score distribution graph 4054; and radial gauges 4056 indicating the relative contribution of a "non-modifiable" risk component and a "modifiable" risk component to the overall risk in various risk categories.

In examples, the system 1000 may be configured to predict the effect of one or more actions by the entire population, or a specific group within the population (e.g. the high risk people), on the average CVD risk score of the population, or the group within the population. For example, if the average CVD risk score of a certain population of 10,000 people is 9%, and everyone in the high risk group were to lower their HbA1c level by 5%, this might make the average CVD score of the entire population 8%.

It is envisaged that this may enable an interested party (e.g. a healthcare provider, insurer, or employer) to predict the impact of certain actions in order to evaluate the relative value of such actions. As an example, the effect of a certain percentage of a high risk group (or subgroup, such as those having a relatively high contribution of risk due to blood pressure) regularly taking blood thinning medication (e.g. aspirin) may be predicted, i.e. if you get X % of the highest risk group to take aspirin, then the overall population CVD risk drops by Y %.

Figure 4D:
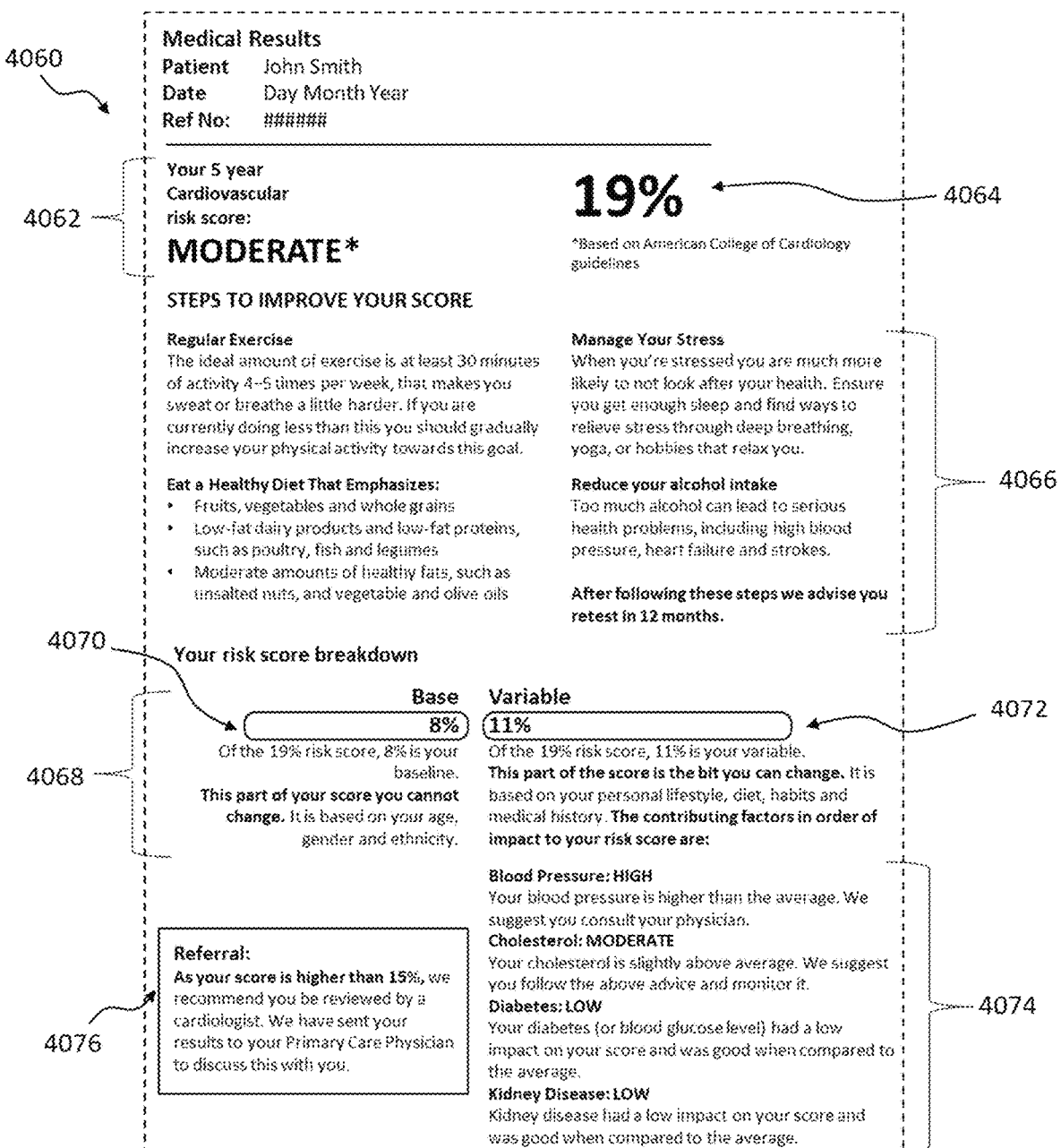
FIG. 4D shows an exemplary report comprising individual-level CVD risk information generated in accordance with aspects of the present technology.

FIG. 4D illustrates another exemplary individual report 4060, comprising an overall risk section 4062 in which the determined CVD risk is presented, comprising an overall risk score 4064 for the individual, in this example presented as a percentage. A recommendation section 4066 summarises key recommendations for the individual to reduce their CVD risk. A risk breakdown section 4068 outlines the base, or non-modifiable, risk contribution 4070, against the variable, or modifiable risk contribution 4072. The respective relative contributions of each contributing factor to the variable risk contribution (e.g. blood pressure, cholesterol, diabetes and kidney disease) are also provided—in this example on a relative scale of low to moderate to high. For instances in which the CVD risk is above a threshold (in this example 15%), a referral recommendation 4076 is included in the report—for example recommending a consultation with a cardiologist.

In examples, one or more of the overall risk, non-modifiable or modifiable risk contributions, and the relative contribution of the modifiable risk factors of an individual may be presented in comparison with values for people in a comparable cohort (e.g. of a similar age, gender, and ethnicity). It is envisaged that doing so may assist an individual with determining if their level of cardiovascular risk is "normal"—i.e. above/below average of their peers.

EXAMPLES

The following description outlines a study undertaken to determine the efficacy of an exemplary prediction method in accordance with the present technology—referred to in this section as "CVD-AI".

Data Preparation

In total, 110,272 fundus images from a database of 55,118 patient visits were used in this study. The dataset was acquired from the UK Biobank and AREDS 1, using approved data management and data transfer protocols.

From the UK Biobank dataset, initially 175,788 macula centered images for both the left and right eyes were acquired. However, due to the prevalence of low-quality images, a deep learning image quality screening system was used to separate the images into high quality, medium quality, and low-quality images. After the screening process there were 95,992 images from 51,956 patients. Due to patients visiting Biobank for repeated assessment visits, there were multiple sets of biometric information per patient. Here, only the earliest images and set of biometrics were used per patient. Dataset processing was also carried out on the AREDS 1 dataset. A similar image screening pre-processing strategy was employed for the AREDS 1 dataset, and the biometric information and fundus images from the first visit only. After screening for image quality, there were 134,476 images from 3,162 patients left for test analysis. To generate a label for the presence or absence of CVD events, ICD10/ICD9 codes were utilized. For the UK Biobank dataset, CVD events were defined based on the "Diagnoses—ICD10" and "Underlying (primary) cause of death: ICD10" fields. For the AREDS dataset, CVD events were defined based on ICD 9 codes from the "ICD9COD1" variable under the "adverse" dataset and the "ICD10" and "ICD9COD1" variables under the mortality dataset.

The UK Biobank dataset (95,992 good quality images from 51,956 patients) was split into 70%:15%:15% for training, validation and testing respectively. For the external test set, AREDS 1 dataset (14,280 good quality images from 3,162 patients) was used.

Model Explainability

To gain a better insight into the behavior of the final multilayer perceptron predictor, the expected gradients algorithm was implemented to estimate the absolute contribution of each of the inputs to the CVD risk multilayer perceptron risk predictor. The expected gradients algorithm estimates an "attribution score" for each of the input fields such as age, gender, systolic blood pressure that are used by the multilayer perceptron risk predictor model to estimate the final CVD risk score. The "attribution score" for an input field, such as age, represents the amount of difference this particular field contributed to the value difference between the predicted CVD risk for this particular patient and that of the entire source dataset. The attribution score for the following key fields were calculated as these factors have been identified as the major contributing factors to an individual cardiovascular risk by the American College of Cardiology: 1. Age, 2. Gender, 3. BMI, 4. Smoking status (represented by model predicted smoking status), 5. Glycemic control (represented by model predicted "effect" of HbA1C) 6. Blood pressure (represented by model predicted "effect" of systolic and Diastolic blood pressure), and 7. Cholesterol/HDL (represented by model predicted "effect" of TCHDL ratio).

The attribution scores for all other input fields into the CVD risk prediction model were categorized and summated under the "others aggregated" category. Due to the uneven magnitudes between the attribution scores for different prediction cases, for example, the attribution scores for a patient with 20% CVD-AI predicted risk will of far greater magnitude when compared to a patient with 12% CVD-AI predicted risk, a scaling algorithm was used to scale the attribution scores between 0 and 100%: scaled attribution percentage$(X_i,X)=(X_i-min(X)/max(X)-min(X))*100$. In this case, X represents the set of attribution scores, and $X_i$ represents an element of the set of attribution scores. Having calculated the attribution scores generated by the modified expected gradients the plausibility of the outputs produced by CVD-AI, based simply on the retinal image, were evaluated in three ways in both the internal validation dataset (Biobank) and the external validation dataset (AREDS 1).

Primary Outcome

Comparison of population based mean and median scores CVD-AI allocated to those individuals who actually experienced a CVD event, compared to those who did not.

Secondary Outcomes

1. By way of comparing the demographics and biometric data of those individuals that CVD-AI categorized as low, medium and high risk; defined by CV risk assessments scores of <5% 5-10% and over 10% respectively. 2. By way of a set of case studies to qualitatively compare the attribution scores generated by CVD-AI to the real-life status of individual patients.

Statistical Analysis

The following statistical methods were applied to analyze the data. The specific method was dependent on the underlying distribution of the data being analyzed: 1. One tailed Mann-Whitney U test for comparison of statistical differences between the means between two non-normally distributed and non-homoscedastic distributions; 2. One tailed Welch's t-test for comparison of means between two non-homoscedastic, but normally distributed distributions; 3. Brown-Forsythe test for homoscedasticity; 4. Shapiro Wilk and D'Agostino-Pearson tests for normality; 5. Contingency table chi-squared tests for comparison of frequencies between groups; 6. Box and whisker plots; 7. Kruskal-Wallis H test for omnibus comparison of means across non-homoscedastic and non-normally distributed groups; 8. Pairwise two tailed Mann-Whitney U tests with p-value correction via the Bonferroni-Holm method for post-hoc analysis following a Kruskal-Wallis H test. Statistical significance was evaluated for the 95% confidence level.

Results

Figure 5A:
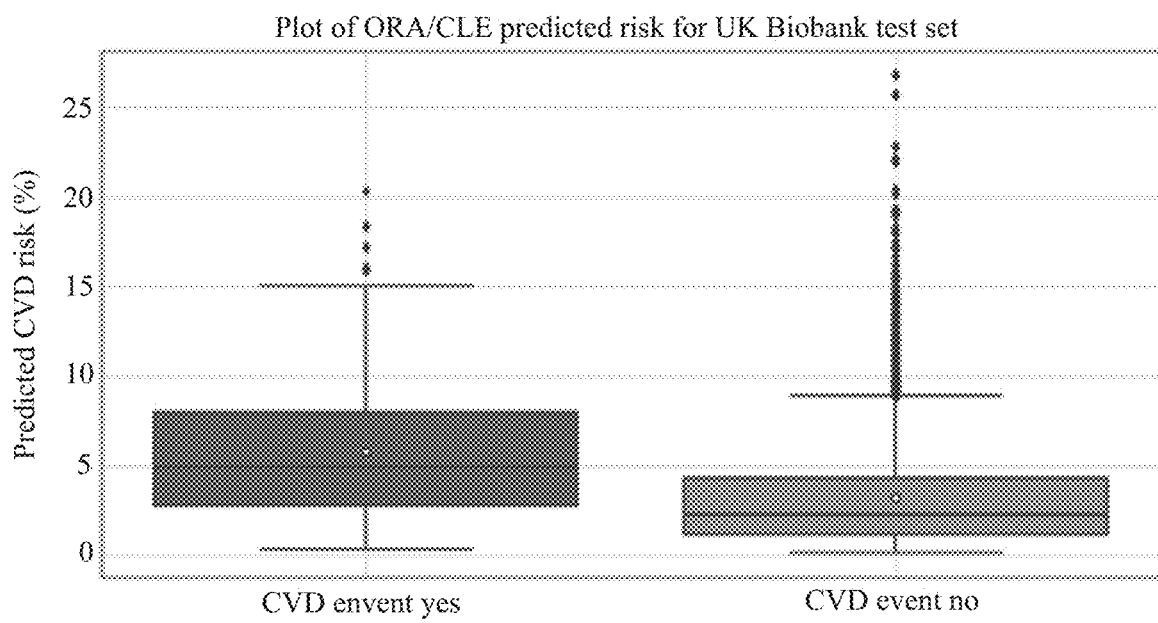
FIG. 5A shows a first plot of predicted CVD risk based on a first dataset in accordance with aspects of the present technology.

In both the UK Biobank testing dataset and the external validation dataset (AREDS 1), the 10-year CV risk scores generated by CVD-AI were significantly higher for patients who had suffered an actual CVD event when compared to patients who did not experience a CVD event. In the Internal validation UK Biobank dataset, the median 10-year CVD risk for those individuals who experienced a CVD was higher than those who did not (4.9% [ICR 2.9-8%] v 2.3% [IQR 4.3-1.3%] P<0.01 one tailed Mann-Whitney U test). Likewise, the mean 10-year CVD risk score for individuals who experienced a CVD event was significantly higher than those who did not (5.8% v 3.3% P<0.01 Welch's t-test). See FIG. 5A: Estimated CVD risk by CVD-AI for people who did vs did not suffer from a CVD event, using the UK Biobank dataset. The center line denotes the median value (50th percentile), while the box contains the 25th to 75th percentiles of dataset. The black whiskers mark the 5th and 95th percentiles, and values beyond these upper and lower bounds are considered outliers. The white circle denotes the mean of the estimated 10-year CVD risk for each category.

Figure 5B:
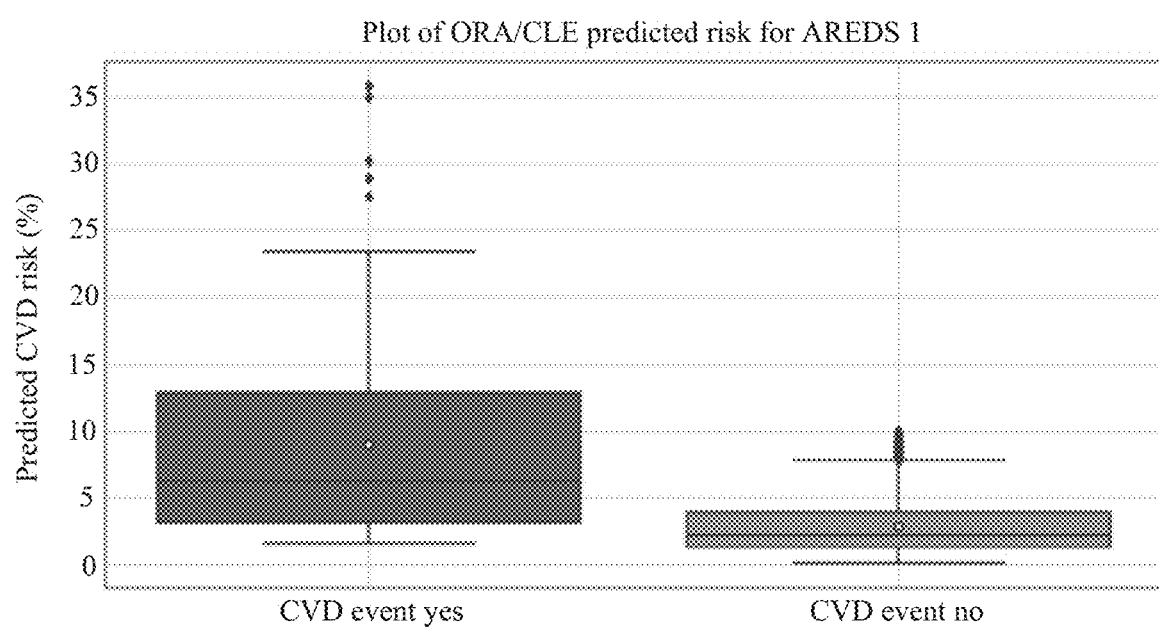
FIG. 5B shows a second plot of predicted CVD risk based on a second dataset in accordance with aspects of the present technology.

Similar results were observed in the AREDS 1 external validation dataset. The median 10-year CVD risk for those individuals who experienced a CVD event was higher than those who did not (6.2% [ICR 3.2%-12.9%] v 2.2% [IQR 3.9-1.3%] P<0.01 one tailed Mann-Whitney U test). Likewise, the mean 10-year CVD risk score for individuals who experienced a CVD event was 9.0%, v 2.9% for those who did not. (P<0.01 Welch's t-test). See FIG. 5B: Estimated CVD risk by CVD-AI for people who did vs did not suffer from a CVD event, using the AREDS 1 dataset. The center line denotes the median value (50th percentile), while the box contains the 25th to 75th percentiles of dataset. The black whiskers mark the 5th and 95th percentiles, and values beyond these upper and lower bounds are considered outliers. The white circle denotes the mean of the estimated 10-year CVD risk for each category.

To further evaluate the relevance of the risk scored calculated by the CVD-AI model, arbitrary cutoff point of 5% was chosen based on the box and whisker plots for both the AREDS 1 and the UK Biobank dataset [33-35]. The 5% threshold divided the patients between a low risk (<5%) and elevated risk (>5%) group. 2×2 Chi-squared tests were then carried out based on the two groups. For the UK Biobank testing dataset, the chi-squared tests $(X^2(7,790, 1)=127.6, p<0.01)$ showed that patients who were assigned elevated risk by the CVD-AI algorithm were significantly more likely to have actual CVD events, and patients who were assigned low risk were less likely to have a CVD event. Similar conclusions were reached on the AREDS 1 dataset, with the 2×2 chi-squared test $(X^2(3,162, 1)=89.1, p<0.01)$ showing similar results.

Metadata Analysis

The UK Biobank and AREDS 1 datasets were then recategorized into three groups based on the 10-year CV risk score allocated by CVD-AI. The following thresholds were used: low risk (<5%), medium risk (5%-10%) and high risk (>10%). The numbers of individuals in each category (Low, Medium, High risk), is summarized in table 1:

|  | CVD-AI issued CVD risk scores <5% (Low) | CVD-AI issued CVD risk scores 5%-10% (Medium) | CVD-AI issued CVD risk scores >10% (High) |
| --- | --- | --- | --- |
| UK Biobank | 6,146 | 1,343 | 301 |
| AREDS 1 | 2,627 | 512 | 23 |

Using the UK Biobank test dataset, a metadata analysis was then conducted on factors such as age, HbA1c, systolic blood pressure (taken as the averaged blood pressure between 2 readings), diastolic blood pressure (taken as the averaged blood pressure between 2 readings), BMI, and the total cholesterol to HDL cholesterol (TCHDL) ratio, categorized by the 10-year CV risk score issued by CVD-AI to individuals within these 3 cohorts. Table 2:

| | Low risk (<5%) | | Medium risk (5-10%) | | High risk (>10%) | | Statistical significance (Yes) |
|---|---|---|---|---|---|---|---|
| | Mean | Standard deviation | Mean | Standard deviation | Mean | Standard deviation | |
| Age (years) | 55 | 8 | 63 | 5 | 67 | 3 | L-H<br>L-M<br>M-H |
| HbA1C (mmol/mol) | 35 | 6 | 37 | 7 | 38 | 8 | L-H<br>L-M |
| Systolic blood pressure (mmHg) | 135 | 18 | 144 | 18 | 143 | 18 | L-H<br>L-M |
| Diastolic blood pressure (mmHg) | 81 | 9.9 | 84 | 9.7 | 81 | 9.5 | L-H<br>L-M |
| BMI | 27. | 4.9 | 28.0 | 4.4 | 28.0 | 4.1 | L-H<br>L-M |
| TCHDL ratio (No units) | 4.0 | 1.0 | 4.1 | 1.0 | 4.0 | 1.2 | L-H<br>L-M |

| | Low risk | Medium Risk | High risk | Statistical significance (Yes) |
|---|---|---|---|---|
| Proportion of men (%) | 33 | 88 | 98 | L-H<br>L-M<br>M-H |
| Proportion of smokers (%) | 41 | 50 | 59 | L-H<br>L-M<br>M-H |
| Proportion of people with diabetes (%) | 3 | 9 | 13 | L-H<br>L-M<br>M-H |

A similar analysis was conducted on the AREDS 1 dataset for the corresponding fields (where available), again categorized by the 10-year risk score allocated by CVD-AI. Table 3:

| | Low risk (<5%) | | Medium risk (5-10%) | | High risk (>10%) | | Statistical significance |
|---|---|---|---|---|---|---|---|
| | Mean | Standard deviation | Mean | Standard deviation | Mean | Standard deviation | |
| Age (years) | 69 | 5 | 70 | 5 | 74 | 5 | L-H<br>L-M<br>M-H |
| Systolic blood pressure (mmHg) | 135 | 17 | 138 | 17 | 144 | 25 | L-M |
| Diastolic blood pressure (mmHg) | 78 | 9 | 78 | 9 | 81 | 10 | |
| BMI | 27 | 5 | 27 | 5 | 30 | 6 | |

| | Low risk | Medium Risk | High risk | Statistical Significance |
|---|---|---|---|---|
| Proportion of men (%) | 40 | 56 | 74 | L-H<br>L-M<br>M-H |
| Proportion of smokers (%) | 51 | 59 | 83 | L-H<br>L-M<br>M-H |
| Proportion of people with diabetes (%) | 8 | 9 | 26 | L-H<br>L-M<br>M-H |

Evaluation of Model Explainability

To qualitatively evaluate CVD-AI's performance and investigate the 'relative contribution' of both non-modifiable factors (age, ethnicity, sex) and modifiable factors (HbA1c, blood pressure, smoking and total cholesterol/HDL cholesterol ratio) on the total estimated 10-year risk score. Eight individual case studies from the high-risk groups were created (5 from the UK Biobank and 3 from AREDS 1). The results of the cases and the relative impact of the component risk factors that comprise this overall risk are summarized in Table 4:

|  | UK Biobank 1 | UK Biobank 2 | UK Biobank 3 | UK Biobank 4 | UK Biobank 5 | AREDS 1 | AREDS 2 | AREDS 3 |
| --- | --- | --- | --- | --- | --- | --- | --- | --- |
| Age | 42 | 63 | 62 | 42 | 75 | 65 | 65 | 67 |
| Gender | M | M | M | M | M | F | M | F |
| BMI | 32 | 37 | 39 | 29 | 31 | 28 | 30 | 27 |
| Smoking status | N | Y | Y | N | N | Y | Y | Y |
| Diabetes status | N | N | Y | Y | Y | N | Y | N |
| Systolic blood pressure (mmHg) | 160 | 160 | 161 | 124 | 134 | 142 | 152 | 220 |
| Diastolic blood pressure (mm/Hg) | 105 | 97 | 76 | 84 | 70 | 80 | 90 | 88 |
| HbA1C (mmol/mol) | 37 | 46 | 62 | 55 | 44 | — | — | — |
| Total cholesterol to HDL cholesterol ratio | 7.1 | 4.8 | 3.0 | 5.2 | 2.7 | — | — | — |
| Total Absolute Risk | 5% | 10% | 22% | 24% | 16% | 8% | 13% | 17% |
| Relative Risk Contribution-Age | <10% | 13% | <10% | 60% | 55% | 26% | <10% | 20% |
| Relative Risk Contribution-Gender | 20% | 27% | <10% | 13% | 33% | 13% | <10% | <10% |
| Relative Risk Contribution-Smoking | <10% | <10% | <10% | <10% | <10% | <10% | <10% | 32% |
| Relative Risk Contribution-Systolic BP | 40% | 17% | <10% | <10% | <10% | 39% | 37% | <10% |
| Relative Risk Contribution-Diabetes | <10% | 12% | 61% | 10% | 10% | <10% | 15% | <10% |
| Relative Risk Contribution-Cholesterol | 20% | 10% | <10% | <10% | <10% | <10% | 40% | 41% |

Discussion

In this study 110,272 fundus images from a database of 55,118 patients from the UK Biobank and AREDS 1 datasets were used to train and subsequently test a novel AI platform (CVD-AI) to calculate a 10-year CVD risk score for these individuals. The predicted risk produced by CVD-AI was compared to the actual cardiovascular event rate to determine the relative accuracy of the prediction so obtained. It was found that CVD-AI could reliably identify patients at high risk of cardiovascular event, most of whom experienced at least one event according to the UK Biobank or AREDS 1 records.

The results are in line with other reports which have demonstrated that deep learning algorithms can use retinal images to predict modifiable CVD risk factors, including diabetes, hypertension, and cholesterol and non-modifiable risk factors such as chronological age and gender. However, like the Framingham equations, the algorithms published to date are unable to examine the relative contribution of each of the individual factors that comprise risk as they utilize a statistical method which imposes linearity between the individual parameters used during analysis. Consequently, these models are trained against a single label like cardiovascular event or chronological age. As such they are incapable of identifying the most significant contributors to CVD risk in any given individual as the math underpinning the algorithm do not account for interactions between the variables that comprise the individuals overall risk. Traditionally, most existing algorithms simply measure success in terms of detection accuracy, where the CVD risk is calculated by conventional equations. For instance, earlier studies report the outcomes of their algorithms in terms of AUC, regarding successful models as those that have an AUC>0.70. Although this approach has its merits merely knowing that a model can predict CVD risk with an AUC>0.70 is of limited value because simply achieving a high level of accuracy does not necessarily mean that the algorithm has learnt what was expected. This is particularly important in the case of biometric data much of which is normally distributed. In data which is normally distributed an algorithm which has simply learnt to assign outputs which are clustered tightly around the mean will, at the population level, be highly accurate. However, in the Real World when presented with individuals whose values fall outside the mean, it will fail to perform.

To assess the biological and Clinical plausibility of CVD-AI this study first evaluated the demographic and biometric data of those individuals allocated to three broad risk categories; low risk (<5%), medium risk (5-10%) and high risk (>10%). These data demonstrated that in both the UK Biobank and AREDS 1 datasets, the demographic and biometric data of the three groups categorized by the results allocated by CVD-AI were largely consistent with traditional cardiovascular risk factors; age gender, smoking, systolic blood pressure and the presence or otherwise of diabetes. However, in addition to the expected traditional metrics other intriguing trends were evident; namely that irrespective of whether the individual had diabetes, HbA1C was significantly and incrementally higher across the 3 groups.

These same trends were observed in the individual case studies. Analysis of these examples again reveal that rising age and male gender were, in the absence of diabetes, the most powerful predictors of cardiovascular risk (Biobank cases 2 & 5, AREDS cases 2 & 3). In contrast, in an older female, systolic hypertension registered more highly than age and gender (AREDS cases 1 & 3). In a younger male patient (Biobank case 1), CVD-AI indicated that the overall risk was low and that in the absence of other CV risk factors, systolic hypertension was the principal factor underpinning this risk. When the individual had diabetes, (Biobank cases 3 & 4, AREDS case 2) blood sugar was one of the principal factors underpinning the individuals CV risk score. However, HbA1C also registered as one of the principle factors underpinning the CV risk score in individuals who did not have diabetes (Biobank case 2 & 5), but whose blood sugar was in the prediabetic range. The finding that HbA1C registers as an important risk factor in patients who don't have diabetes, but whose blood sugar is in the pre diabetic "normal" range is intriguing. Mean HbA1C was also significantly higher in patients who CVD-AI allocated medium and high-risk scores compared to those allocated low-risk scores. It is well recognized that individuals with prediabetes are at increased risk of not only developing type 2 diabetes, but are also at an increased risk of experiencing a CV event. It is thus possible that CVD-AI is detecting a change within the retina that allows it to discern this subtle signal. As CVD-AI was not trained to predict the HbA1C, this information must instead be derived from as yet unknown changes in the retinal that results from raised; but "normal" glucose levels. It has recently been reported in prediabetic rat models that elevated, but non diabetic, glucose levels are associated with activation of the TRVP-2 pathway and retinal arteriolar dilation. Although further work in this area is required, results may indicate that a similar process may be at work in the retina of humans with prediabetes.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the field of endeavour in any country in the world.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The present disclosure may also be said broadly to consist in the parts, elements and features referred to or indicated in the specification of the application, individually or collectively, in any or all combinations of two or more of said parts, elements or features. Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the present disclosure and without diminishing its attendant advantages. It is therefore intended that such changes and modifications be included within the present disclosure as defined by the appended claims.

The invention claimed is:

1. A method of predicting a risk of cardiovascular disease (CVD) from one or more fundus images, the method performed by one or more processors, the method comprising:
    processing one or more fundus images associated with an individual using a Quality Assurance (QA) set of one or more convolutional neural networks (CNNs) to determine whether the one or more fundus images are of sufficient quality for further processing;
    processing the one or more fundus images determined to be of sufficient quality for further processing using an eye-identification set of one or more CNNs (eye-ID CNN), to identify the one or more fundus images belonging to a single eye;
    processing the one or more fundus images using a plurality of risk contributing factor sets of one or more CNNs (RCF CNN), wherein each RCF CNN is configured to output an indicator of probability of the presence of a different risk contributing factor in each of the one or more fundus images,
        wherein at least one of the RCF CNNs is configured in a jury system model comprising a plurality of jury member CNNs, wherein each jury member CNN is configured to output a probability of a different feature in the one or more fundus images, and the outputs of the plurality of jury member CNNs are processed to determine the indicator of probability of the presence of the risk contributing factor output by the RCF CNN;
    producing an individual feature vector based on meta-information for the individual, and the outputs of the plurality of RCF sets of one or more CNNs;
    processing the individual feature vector using a CVD risk prediction neural network model to output a prediction of overall CVD risk for the individual, wherein the CVD risk prediction neural network model is configured to determine a relative contribution of each of the risk contributing factors to the prediction of overall CVD risk; and
    reporting the overall CVD risk, comprising reporting the relative contribution of each of the risk contributing factors to the overall CVD risk.

2. The method of claim 1, wherein the one or more contributing factors comprise one or more non-modifiable contributing factors, and one or more modifiable contributing factors.

3. The method of claim 2, further comprising providing at least one recommendation for management of an individual's condition based on the CVD risk, wherein the at least one recommendation is provided based on the relative contribution of each modifiable contributing factor.

4. The method of claim 1, further comprising:
    comparing at least one of the overall CVD risk, and the relative contribution of each of the risk contributing factors to the overall CVD risk, of the individual to at least a portion of a population of individuals for whom the overall CVD risk is predicted by the CVD risk prediction neural network model; and
    reporting an indication of the comparison.

5. The method of claim 1, further comprising predicting a change to the overall CVD risk based on a change to one or more of the risk contributing factors.

6. The method of claim 1, further comprising determining a prediction of group overall CVD risk for at least a portion of a population of individuals for whom the overall CVD risk is predicted by the CVD risk prediction neural network model.

7. The method of claim 6, further comprising predicting a change to the group overall CVD risk based on a change to one or more of the risk contributing factors for at least a portion of the population of individuals.

8. The method of claim 1, wherein determining whether the one or more fundus images is suitable comprises one or more of: determining whether the fundus image is directed to a relevant region of an eye of the individual, and determining whether at least one property of the image is unsuitable.

9. The method of claim 8, further comprising issuing a notification warning a user that the one or more fundus images supplied are unsuitable.

10. The method of claim 1, wherein the one or more fundus images comprise a plurality of fundus images, and the method comprises processing the plurality of fundus images using the eye-ID CNN to group each of the plurality fundus images as belonging to a single eye.

11. The method of claim 1, comprising adjusting the one or more fundus images prior to processing with the RCF CNNs.

12. The method of claim 11, wherein the adjusting of the one or more fundus images comprises one or more of: normalisation of the images, performing a color balancing process, and performing a brightness adjustment process.

13. The method of claim 11, comprising determining whether the device used to capture each of the one or more fundus images utilised flash photography or white LED confocal photography, wherein the adjusting of the one or more fundus images prior to processing is based at least in part on the determination of whether flash photography or white LED confocal photography was utilised.

14. The method of claim 1, wherein the risk contributing factors comprise two or more of: glycaemic control, blood pressure, cholesterol, and exposure to smoking.

15. The method of claim 1, wherein the outputs from the RCF CNNs are aggregated to generate an individual-level fundus image feature vector.

16. The method of claim 15, wherein the meta-information of the individual is processed to generate a meta-information vector, and the meta-information vector is combined with the individual-level fundus image feature vector to produce the individual feature vector.

17. The method of claim 16, wherein the meta-information is pre-processed using one or more of standardisation and one-shot encoding.

18. The method of claim 1, wherein the outputs of the plurality of jury member CNNs are processed to determine the indicator of probability of the presence of the risk contributing factor output by the RCF CNN based on an expected population baseline for a population to which the individual belongs.

19. A system for predicting a risk of cardiovascular disease (CVD) from one or more fundus images, the system comprising comprising one or more processors and one or more storage devices storing instructions that when executed by the one or more processors cause the one or more processors to perform operations comprising:
   processing one or more fundus images associated with an individual using a Quality Assurance (QA) set of one or more convolutional neural networks (CNNs) to determine whether the one or more fundus images are of sufficient quality for further processing;
   processing the one or more fundus images determined to be of sufficient quality for further processing using an eye-identification set of one or more CNNs (eye-ID CNN), to identify the one or more fundus images belonging to a single eye;
   processing the one or more fundus images using a plurality of risk contributing factor sets of one or more CNNs (RCF CNN), wherein each RCF CNN is configured to output an indicator of probability of the presence of a different risk contributing factor in each of the one or more fundus images,
      wherein at least one of the RCF CNNs is configured in a jury system model comprising a plurality of jury member CNNs, wherein each jury member CNN is configured to output a probability of a different feature in the one or more fundus images, and the outputs of the plurality of jury member CNNs are processed to determine the indicator of probability of the presence of the risk contributing factor output by the RCF CNN;
   producing an individual feature vector based on meta-information for the individual, and the outputs of the plurality of RCF sets of one or more CNNs;
   processing the individual feature vector using a CVD risk prediction neural network model to output a prediction of overall CVD risk for the individual, wherein the CVD risk prediction neural network model is configured to determine a relative contribution of each of the risk contributing factors to the prediction of overall CVD risk; and
   reporting the overall CVD risk, comprising reporting the relative contribution of the risk contributing factors to the overall CVD risk.

20. A computer program product for predicting a risk of cardiovascular disease (CVD) from one or more fundus images, the computer program product comprising a non-transitory computer-readable storage medium containing computer program code for:
   processing one or more fundus images associated with an individual using a Quality Assurance (QA) set of one or more convolutional neural networks (CNNs) to determine whether the one or more fundus images are of sufficient quality for further processing;
   processing the one or more fundus images determined to be of sufficient quality for further processing using an eye-identification set of one or more CNNs (eye-ID CNN), to identify the one or more fundus images belonging to a single eye;
   processing the one or more fundus images using a plurality of risk contributing factor sets of one or more CNNs (RCF CNN), wherein each RCF CNN is configured to output an indicator of probability of the presence of a different risk contributing factor in each of the one or more fundus images,
      wherein at least one of the RCF CNNs is configured in a jury system model comprising a plurality of jury member CNNs, wherein each jury member CNN is configured to output a probability of a different feature in the one or more fundus images, and the outputs of the plurality of jury member CNNs are processed to determine the indicator of probability of the presence of the risk contributing factor output by the RCF CNN;
   producing an individual feature vector based on meta-information for the individual, and the outputs of the plurality of RCF sets of one or more CNNs;
   processing the individual feature vector using a CVD risk prediction neural network model to output a prediction of overall CVD risk for the individual, wherein the CVD risk prediction neural network model is configured to determine a relative contribution of each of the risk contributing factors to the prediction of overall CVD risk; and
   reporting the overall CVD risk, comprising reporting the relative contribution of the risk contributing factors to the overall CVD risk.

* * * * *